US00PP28141P3

(12) United States Plant Patent
Gray

(10) Patent No.: US PP28,141 P3
(45) Date of Patent: Jun. 27, 2017

(54) ***HYDRANGEA* PLANT NAMED 'MOTHER'S LOVE'**

(50) Latin Name: *Hydrangea macrophylla*
Varietal Denomination: Mother's Love

(71) Applicant: Carol Gray, Davis, CA (US)

(72) Inventor: Joseph Gray, Davis, CA (US)

( * ) Notice: Subject to any disclaimer, the term of this patent is extended or adjusted under 35 U.S.C. 154(b) by 30 days.

(21) Appl. No.: 14/998,559

(22) Filed: Jan. 19, 2016

(65) Prior Publication Data

US 2016/0249510 P1 Aug. 25, 2016

Related U.S. Application Data

(60) Provisional application No. 62/176,491, filed on Feb. 19, 2015.

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Audrey Charles

(57) ABSTRACT

A new cultivar of *Hydrangea macrophylla* named 'Mother's Love' that is characterized by its compact plant habit with tight internodes, its extremely floriferous bloom period, re-blooming through the spring and summer months, its profusion of light pink florets that often crowd out the foliage, and its extreme heat tolerance, regularly tolerating temperatures of 38° C. in the summer.

1 Drawing Sheet

Latin name of genus and species of plant claimed: *Hydrangea macrophylla.*

Varietal denomination: 'Mother's Love'.

BACKGROUND OF THE INVENTION

The present invention relates to a new and distinct cultivar of *Hydrangea macrophylla* and will be referred to hereafter by its cultivar name, 'Mother's Love'. 'Mother's Love' represents a new mophead type *Hydrangea*, a deciduous shrub grown for landscape use and for use as a potted plant.

The new cultivar of *Hydrangea* arose from a controlled breeding program conducted by the Inventor in Davis, Calif., USA. The Inventor made a cross in May 2008 between a proprietary plant in the Inventor's breeding program coded 060973, as the female parent and a proprietary plant in the Inventor's breeding program coded 068013 as the male parent. The Inventor selected 'Mother's Love' in May 2009, as a single unique plant amongst the seedlings that resulted from the above cross.

Asexual propagation of the new cultivar was first accomplished by the Inventor by one and two node tip cuttings in Davis, Calif., in July 2009. Asexual propagation by tip stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Mother's Love' as a unique cultivar of *Hydrangea.*

1. 'Mother's Love' exhibits a compact plant habit with tight internodes.

2. 'Mother's Love' exhibits an extremely floriferous bloom period, re-blooming through the spring and summer months.
3. 'Mother's Love' exhibits a profusion of light pink florets that often crowd out the foliage.
4. 'Mother's Love' exhibits extreme heat tolerance, regularly tolerating temperatures of 38° C. in the summer.

The female parent of 'Mother's Love' differs from 'Mother's Love' in being a lacecap type *Hydrangea*. The male parent of 'Mother's Love' differs from 'Mother's Love' in having fewer total florets per bloom cycle.

'Mother's Love' can be most closely compared to the *Hydrangea* cultivars 'Endless Summer' (U.S. Plant Pat. No. 15,298) and 'All Summer Beauty' (not patented). Both cultivars are similar in being re-bloom, mophead type *Hydrangeas*. 'Endless Summer' differs from 'Mother's Love' in having a smaller bud count, in being less heat tolerant, in being less vigorous in nursery production, and in being more prone to flopping under normal shade house growing conditions. 'All Summer Beauty' differs from 'Mother's Love' in being less heat tolerant and in having fewer total florets per bloom cycle.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs may differ slightly from the color values cited in the detailed description, which accurately describes the colors of 'Mother's Love'. The plants were approximately one-year old and were grown to flowering stage in one-gallon containers for 3 months in West Chicago, Ill.

DETAILED BOTANICAL DESCRIPTION

Figure 1:
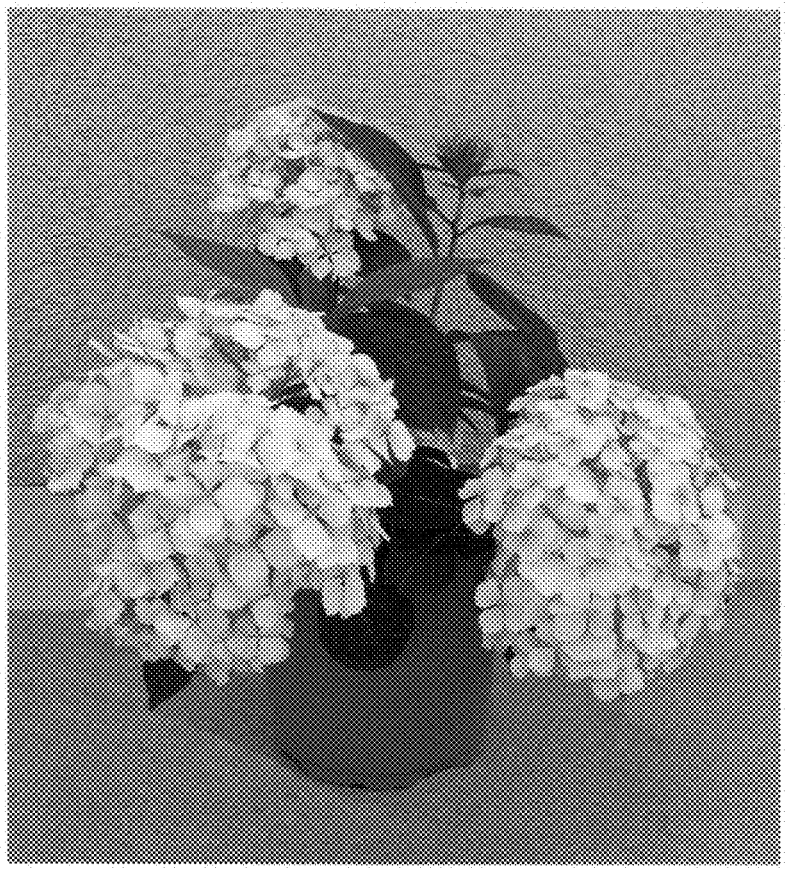
FIG. 1 illustrates a side view of the overall growth and flowering habit of 'Mother's Love'.
Figure 2:
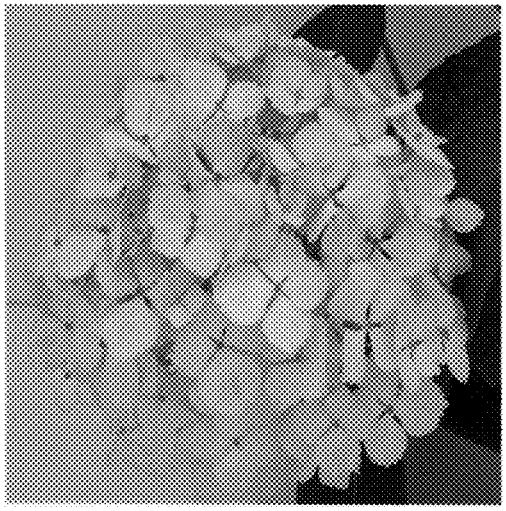
FIG. 2 illustrates a close-up view of the inflorescence of 'Mother's Love' showing floret color when first open.
Figure 3:
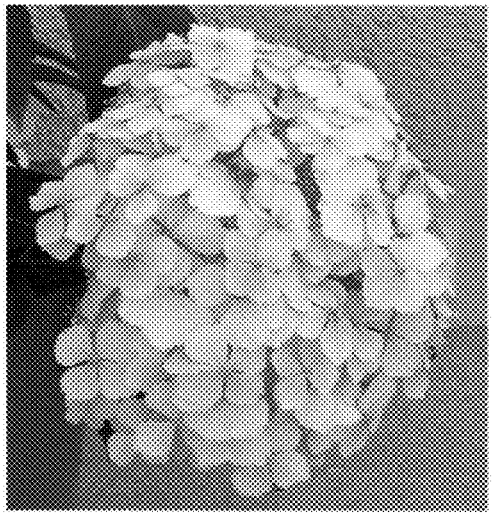
FIG. 3 illustrates a close-up view of a fully-open inflorescence of 'Mother's Love'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The Royal Horticultural Society Colour Chart of The Royal Horticultural Society, London, England, 2007 edition, except where general color terms of ordinary significance are used. The color values were determined in May 2015 under natural light conditions in West Chicago, Ill.

The following descriptions and measurements describe approximately one-year old plants produced from cuttings from stock plants and grown in a greenhouse under conditions comparable to those used in commercial practice. Plants were pinched when transplanted into a soilless growth medium in one-gallon containers and maintained under an average day temperature of 45° F. (7.2° C.) and an average night temperature of 35° F. (1.7° C.). The plants were then grown for three months in West Chicago, Ill. with greenhouse temperatures maintained at approximately 60° F. to 65° F. (15.5° C. to 18.3° C.) during the day and approximately 55° F. to 60° F. (12.7° C. to 15.5° C.) during the night. No supplemental lighting was provided. Measurements and numerical values represent averages of typical plants.

Botanical classification: *Hydrangea macrophylla* cultivar Mother's Love.

Parentage:

*Female parent*.—Proprietary *Hydrangea macrophylla* breeding selection coded 060973, not patented.

*Male parent*.—Proprietary *Hydrangea macrophylla* breeding selection coded 068013, not patented.

Propagation:

*Type cutting*.—Terminal stem.

*Time to initiate roots*.—Approximately 14 to 21 days.

*Time to produce a rooted cutting*.—Approximately 21 to 28 days.

*Root description*.—White dense, medium thickness.

*Rooting habit*.—Freely branching.

Plant description:

*Commercial crop time*.—Approximately 10 months from a rooted cutting to finish in an 15 cm pot.

*Growth habit and general appearance*.—Deciduous shrub, mophead type *Hydrangea*. Moderately vigorous. Compact with tight internodes.

*Hardiness*.—USDA Zone 5 (−20° F. to −15° F.).

*Heat tolerance*.—Regularly tolerates temperatures as high as 38° C. in the summer.

*Size*.—Height from soil level to top of plant plane: Approximately 25.0 cm. Width: Approximately 41.0 cm.

*Branching habit*.—Freely branching. Pinching enhances branching. Quantity of lateral branches per plant: Approximately 4.

*Branch*.—Shape: Rounded. Strength: Strong. Length to base of inflorescence: Approximately 16.0 cm. Diameter: Approximately 4.0 mm. Length of central internode: Approximately 7.0 cm. Texture of young stem: Glabrous. Texture of mature stem: Woody. Color of young stem: 144B. Color of mature stem: Closest to 199A.

*Lenticels*.—Quantity per internode: Approximately 45. Shape: Round to elliptic. Size: Approximately 1.0 to 2.0 mm. Color: N186A.

Foliage description:

*General description*.—Quantity of leaves per lateral branch: Approximately 8 (4 pairs). Fragrance: None detected. Form: Simple. Arrangement: Opposite.

*Leaves*.—Aspect: Flat. Shape: Elliptic. Margin: Serrated. Apex: Acuminate. Base: Cuneate. Venation pattern: Pinnate. Length of mature leaf: Approximately 15.0 cm. Width of mature leaf: Approximately 7.0 cm. Texture of upper and lower surfaces: Coriaceous, glabrous. Color of upper surface of young foliage: 137A blended with 144A, venation of 145C. Color of lower surface of young foliage: Closest to but with more yellow than 138B, venation of 145C. Color of upper surface of mature foliage: N137A blended with 139A and tinted with 187A, venation of 147D. Color of lower surface of mature foliage: Closest to 147B, venation of 145C.

*Petiole*.—Length: Approximately 2.5 cm. Diameter: Approximately 3.0 mm. Texture: Glabrous. Color: 147C with an overlay of 187A.

Flowering description:

*Flowering habit*.—Seasonal, May through August.

*Lastingness of individual inflorescence on the plant*.—Approximately one month.

Inflorescence description:

*General description*.—Type: Terminal globular, mophead, compound corymb of fertile florets and rotate-shaped, sterile, sepalous florets borne on the same corymb, persistent. Sterile florets occasionally have visible reproductive parts, but lack an ovary. Quantity per plant: Approximately 4. Fragrance: Slight. Aspect: Face upward and outward. Height: Approximately 10.0 to 14.0 cm. Width: Approximately 18.0 cm. Quantity of fertile florets per inflorescence: Approximately 17. Quantity of sterile florets per inflorescence: Approximately 150.

*Peduncle*.—Strength: Strong. Shape: Rounded. Length: Approximately 2.5 cm. Diameter: Approximately 4.0 mm. Texture: Sparsely pubescent with appressed hairs. Color: 144B with an overlay of 187A.

Floret description:

*General description*.—Type: Single, sterile and fertile.

*Sterile florets, bud just before opening*.—Shape: Globular. Length: Approximately 3.0 mm. Diameter: Approximately 3.0 mm. Color: 145B with an overlay of 187A on distal end.

*Sterile florets*.—Depth: Approximately 3.0 mm, or 1.0 cm if reproductive parts observed. Diameter: Approximately 4.0 cm. Corolla: 4 petals, often closed forming a central eye. Shape: Rotate, cruciform. Diameter: Approximately 7.0 mm. Calyx: 4 sepals. Shape: Rotate, cruciform. Diameter: Approximately 4.0 cm.

*Petals, sterile florets*.—Shape: Ovate when open, otherwise petals form a center eye of up to 2.0 mm in diameter and 75A in color. Margin: Entire. Apex: Acute. Base: Truncate. Length: Approximately 3.0 mm. Width: Approximately 2.0 mm. Texture of upper and lower surfaces: Glabrous. Color of upper and lower surfaces: NN155A with an overlay of 75A.

*Sepals, sterile florets*.—Shape: Broadly obovate. Margin: Crenate. Apex: Rounded. Base: Attenuate. Length: Approximately 2.0 cm. Width: Approximately 1.5 to 2.0 cm. Texture of upper and lower surfaces: Glabrous. Color of upper surface when first open: 145C with an overlay of 75C that extends from sepal margins to base during development. Color of lower surface when first open: 145D with an overlay of 75D that extends from sepal margins to base during development. Color of upper surface when fully open: 75D transitioning to base of 75A. Color of lower surface when fully open: 75D with base and venation of 75B.

*Pedicel, sterile florets*.—Strength: Strong. Aspect: Approximately 45° from peduncle axis. Length: Approximately 2.5 cm. Diameter: Approximately 1.0 mm. Texture: Sparsely pubescent with appressed hairs. Color: 77C.

*Fertile florets, bud just before opening*.—Shape: Globular. Length: Approximately 3.0 mm. Diameter: Approximately 3.0 mm. Color: 75A.

*Fertile florets*.—Depth: Approximately 9.0 mm. Diameter: Approximately 1.0 cm. Corolla: 4 to 5 petals, often vestigial. Shape: Rotate. Diameter: Approximately 9.0 mm. Calyx: Up to 6 vestigial sepals. Shape: Rotate. Diameter: Approximately 5.0 mm.

*Petals, fertile florets*.—Shape: Ovate. Margin: Entire. Apex: Acute. Base: Truncate. Length: Approximately 4.0 mm. Width: Approximately 3.0 mm. Texture of upper and lower surfaces: Glabrous. Color of upper and lower surfaces: NN155A with an overlay of 75A.

*Sepals, fertile florets*.—Shape: Ovate. Margin: Serrate. Apex: Acute. Base: Truncate. Length: Approximately 2.0 mm. Width: Approximately 1.0 mm. Texture of upper surface: Glabrous. Texture of lower surface: Sparsely pubescent. Color of upper and lower surfaces: 145B with an overlay of 72A.

*Pedicel, fertile florets*.—Strength: Strong. Aspect: Erect. Length: Approximately 3.0 mm. Diameter: Approximately 1.0 mm. Texture: Sparsely pubescent with appressed hairs. Color: 77C.

*Reproductive organs*.—Observed in fertile florets and occasionally in the center of sterile florets, sterile florets lack an ovary. Androecium: Stamen quantity: 6 to 10 per floret. Stamen length: Approximately 6.0 mm to 9.0 mm. Filament color: 72B. Anther shape: Kidney-shaped, basally attached. Anther length: Approximately 1.0 mm. Anther color: NN155A with an overlay of 72B. Pollen amount: Abundant. Pollen color: NN155A. Gynoecium: Pistil quantity: 1 per floret. Pistil length: Approximately 5.0 mm. Stigma shape: Round. Stigma color: 72B. Style length: Approximately 2.0 mm, three-lobed. Style color: 75A with an overlay of 72B. Ovary length: Approximately 3.0 mm. Ovary texture: Sparsely pubescent with appressed hairs. Ovary color: 75A.

Seed and fruit production: Neither seed nor fruit production has been observed.

Disease and pest resistance: Has been observed to be powdery mildew free under the conditions grown.

What is claimed is:

1. A new and distinct cultivar of *Hydrangea* plant named 'Mother's Love' substantially as herein illustrated and described.

* * * * *